(12) United States Patent
Choi et al.

(10) Patent No.: US 11,490,822 B2
(45) Date of Patent: Nov. 8, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Mok Choi, Suwon-si (KR); Jeong Eun Hwang, Suwon-si (KR); Byung Hoon Ko, Hwaseong-si (KR); Jong Wook Lee, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 134 days.

(21) Appl. No.: 16/813,887

(22) Filed: Mar. 10, 2020

(65) Prior Publication Data

US 2020/0390346 A1 Dec. 17, 2020

(30) Foreign Application Priority Data

Jun. 12, 2019 (KR) .................. 10-2019-0069300

(51) Int. Cl.
*A61B 5/021* (2006.01)
*A61B 5/00* (2006.01)
*A61B 5/316* (2021.01)

(52) U.S. Cl.
CPC .......... *A61B 5/02116* (2013.01); *A61B 5/316* (2021.01); *A61B 5/681* (2013.01); *A61B 5/6803* (2013.01); *A61B 5/6843* (2013.01); *A61B 5/725* (2013.01); *A61B 5/7264* (2013.01); *A61B 2562/02* (2013.01)

(58) Field of Classification Search
CPC ... A61B 5/02116; A61B 5/316; A61B 5/6803; A61B 5/681; A61B 5/6843; A61B 5/725; A61B 5/7264; A61B 2562/02
See application file for complete search history.

(56) References Cited

U.S. PATENT DOCUMENTS

| | | |
|---|---|---|
| 2006/0058691 A1 | 3/2006 | Kiani |
| 2010/0087720 A1 | 4/2010 | Addison |
| 2012/0232359 A1 | 9/2012 | Al-Ali et al. |
| 2014/0163344 A1 | 6/2014 | Al-Ali |

(Continued)

FOREIGN PATENT DOCUMENTS

| | | |
|---|---|---|
| CN | 106255449 A | 12/2016 |
| EP | 3 473 170 A1 | 4/2019 |

(Continued)

OTHER PUBLICATIONS

Communication dated Oct. 14, 2020 issued by the European Patent Office in European Application No. 20170027.5.

*Primary Examiner* — Daniel L Cerioni
(74) *Attorney, Agent, or Firm* — Sughrue Mion, PLLC

(57) ABSTRACT

An apparatus for estimating bio-information includes a pulse wave sensor configured to measure a pulse wave signal from an object, for a predetermined period of time, a processor configured to extract DC components of the pulse wave signal measured for the predetermined period of time, normalize the extracted DC components, based on at least one of the extracted DC components of the pulse wave signal measured at a time when a reference force is applied by the object to the pulse wave sensor, and estimate the bio-information, based on the normalized DC components.

24 Claims, 10 Drawing Sheets

(56) References Cited

U.S. PATENT DOCUMENTS

| | | | |
|---|---|---|---|
| 2014/0213913 A1 | 7/2014 | Parfenova et al. | |
| 2014/0316292 A1 | 10/2014 | McRae et al. | |
| 2015/0182172 A1 | 7/2015 | Shelley et al. | |
| 2015/0366492 A1 | 12/2015 | De Haan et al. | |
| 2017/0156606 A1* | 6/2017 | Ferber | A61B 5/14539 |
| 2017/0319146 A1 | 11/2017 | Park et al. | |
| 2018/0132736 A1* | 5/2018 | Silverman | A61B 5/0261 |
| 2019/0104997 A1* | 4/2019 | Kang | A61B 5/022 |
| 2019/0110758 A1 | 4/2019 | Kang et al. | |
| 2019/0125198 A1 | 5/2019 | Kang et al. | |

FOREIGN PATENT DOCUMENTS

| | | |
|---|---|---|
| EP | 3 476 280 A1 | 5/2019 |
| KR | 10-2020-0097143 A | 8/2020 |

\* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0069300, filed on Jun. 12, 2019, in the Korean Intellectual Property Office, the disclosure of which is incorporated herein by reference in its entirety.

BACKGROUND

1. Field

Apparatuses and methods consistent with example embodiments relate to estimating bio-information, and more particularly to technology for cufflessly measuring blood pressure.

2. Description of the Related Art

Methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is a cuff-based blood pressure measurement method, in which a pressure in a cuff wound around an upper arm is increased and blood pressure is measured by listening to the sound generated in the blood vessel through a stethoscope while decreasing the pressure of the cuff on the upper arm. Another cuff-based blood pressure measurement method is an oscillometric method that uses an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods include a method of estimating blood pressure by calculating a Pulse Transit Time (PTT), and a Pulse Wave Analysis (PWA) method for estimating blood pressure by analyzing a pulse wave shape.

SUMMARY

According to an aspect of an example embodiment, there is provided an apparatus for estimating bio-information, the apparatus including a pulse wave sensor configured to measure a pulse wave signal from an object, for a predetermined period of time, a processor configured to extract DC components of the pulse wave signal measured for the predetermined period of time and normalize the extracted DC components, based on at least one of the extracted DC components of the pulse wave signal measured at a time when a reference force is applied by the object to the pulse wave sensor, and estimate the bio-information, based on the normalized DC components.

The pulse wave sensor may further include a light source configured to emit light onto the object that is in contact with the pulse wave sensor and a detector configured to detect light that is reflected from the object.

The apparatus for estimating bio-information may further include a force sensor configured to measure a force that is applied by the object to the pulse wave sensor, for the predetermined period of time.

The processor may be further configured to extract the DC components by passing the measured pulse wave signal through a low-pass filter.

The processor may be further configured to obtain the normalized DC components by dividing the extracted DC components of the pulse wave signal measured at each time during the predetermined period of time by at least one of the extracted DC components of the pulse wave signal measured at the time when the reference force is applied.

The processor may be further configured to obtain the normalized DC components by subtracting at least one of the extracted DC components of the pulse wave signal measured at the time when the reference force is applied from the extracted DC component of the pulse wave signal measured at each time during the predetermined period of time.

The processor may be further configured to estimate the bio-information, based on the normalized DC components and a bio-information estimation model.

The bio-information may include any one or any combination of a blood pressure, a vascular age, an arterial stiffness, an aortic pressure waveform, a vascular compliance, a stress index, and a degree of fatigue.

The processor may be further configured to determine at least one DC component among the normalized DC components, and estimate the bio-information, using at least one of the determined DC components.

The processor may be further configured to determine, among the normalized DC components, as a DC component for use in estimating the bio-information, any one or any combination of a DC component having a maximum intensity, a DC component at a predetermined time after the time when the reference force is applied, a DC component at a time when a predetermined force is applied after the time when the reference force is applied, and a DC component corresponding to a point at which an amplitude of the measured pulse wave signal is at a maximum.

The processor may further be configured to estimate the bio-information by using a force value applied by the object to the pulse wave sensor at the time when the amplitude of the measured pulse wave signal is at a maximum.

The processor may be further configured to guide either one or both of a position of the pulse wave sensor to be contacted by the object, and a force to be applied by the object to the pulse wave sensor for the predetermined period of time.

The apparatus for estimating bio-information may further include an output configured to output the estimated bio-information.

According to an aspect of another example embodiment, there is provided a method of estimating bio-information, the method including measuring a pulse wave signal from an object for a predetermined period of time, extracting DC components of the pulse wave signal measured for the predetermined period of time, and normalizing the extracted DC components, based on at least one of the extracted DC components of the pulse wave signal measured at a time when a reference force is applied by the object to a pulse wave sensor, and to estimate the bio-information, based on the normalized DC components.

In addition, the method of estimating bio-information may further include measuring a force applied by the object to the pulse wave sensor for the predetermined period of time.

The obtaining of the normalized DC components may be configured to include obtaining the normalized extracted DC components by dividing the extracted DC components of the pulse wave signal measured at each time during the predetermined period of time by at least one of the extracted DC components of the pulse wave signal measured at the time when the reference force is applied.

The obtaining of the normalized DC components may further be configured to include obtaining the normalized DC components by subtracting at least one of the extracted DC components of the pulse wave signal measured at the time when the reference force is applied from the extracted DC components of the pulse wave signal measured at each time during the predetermined period of time.

The method of estimating bio-information may further include estimating the bio-information based on the normalized DC components and a bio-information estimation model.

The estimating of the bio-information may further be configured to include determining at least one DC component among the normalized DC components and estimating the bio-information using the determined DC component.

The determining of the DC component may include determining, as a DC component for use in estimating the bio-information among the normalized DC components, any one or any combination of a DC component having a maximum intensity, a DC component at a predetermined time after the time when the reference force is applied, a DC component at a time when a predetermined force is applied after the time when the reference force is applied, and a DC component corresponding to a point at which an amplitude of the measured pulse wave signal is at a maximum.

The estimating of the bio-information may further be configured to include estimating the bio-information by using a force value applied by the object to the pulse wave sensor at the time when the amplitude of the pulse wave signal is at a maximum.

The processor may be further configured to monitor a health condition of a user, based on the estimated bio information and output warning information based on the monitored health condition.

The apparatus for estimating bio-information may further include an image sensor configured to capture an image of the object, wherein the processor is further configured to, based on the captured image, identify a relative position of the object with respect to an actual position of the pulse wave sensor and provide the identified relative position of the object to guide a user to contact the pulse wave sensor with the object.

According to an aspect of another example embodiment, there is provided a non-transitory computer-readable storage medium comprising instructions to cause a processor to measure a force that is applied by an object to a pulse wave sensor, for a predetermined period of time, measure a pulse wave signal from the object, for the predetermined period of time, using the pulse wave sensor, extract DC components of the pulse wave signal measured for the predetermined period of time, normalize the extracted DC components, using one of the extracted DC components of the pulse wave signal measured at a time when the measured force is greater than or equal to a reference force, estimate the bio-information, based on the normalized DC components and output the estimated bio-information estimation.

BRIEF DESCRIPTION OF THE DRAWINGS

The above and/or other aspects will be more apparent from the following description of example embodiments taken in conjunction with the accompanying drawings, in which.

DETAILED DESCRIPTION

Figure 1:
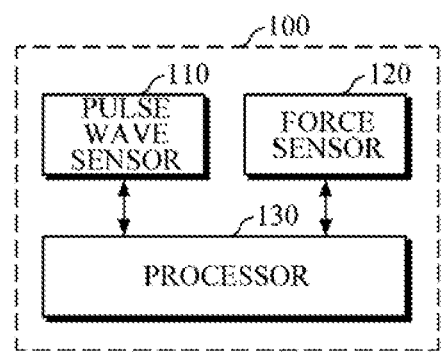
FIG. 1 is a block diagram illustrating an apparatus for estimating bio-information according to an example embodiment.

Details of example embodiments are included in the following detailed description and drawings. Advantages and features of the example embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising", will be understood to imply the inclusion of stated elements but not the exclusion of any other elements. Terms, such as 'part' and 'module' denote units that process at least one function or operation and they may be implemented by using hardware, software, or a combination thereof.

Hereinafter, example embodiments of an apparatus and method for estimating bio-information will be described in detail with reference to the accompanying drawings.

Various example embodiments of the apparatus for estimating bio-information, which will be described below, may be embedded in various devices such as a mobile wearable device, a smart device, and the like. Examples of various devices may include, but are not limited to, various types of wearable devices such as a smartwatch worn on the wrist, a smart band-type wearable device, a headphone-type wearable device, a headband-type wearable device, and the like, or mobile devices such as a smartphone, a tablet PC, and the like.

FIG. 1 is a block diagram illustrating an apparatus for estimating bio-information according to an example embodiment.

Referring to FIG. 1, the apparatus 100 for estimating bio-information includes a pulse wave sensor 110, a force sensor 120, and a processor 130.

The pulse wave sensor 110 may measure continuous pulse wave signals, including a photoplethysmography (PPG)

signal, from an object for a predetermined period of time. The object may be skin tissue of the human body, and may be, for example, a body part such as the back of the hand, the wrist, fingers, and the like, at which veins or capillaries are located. However, the object is not limited thereto, and may be a body part at which arteries, such as the radial artery, are located.

The pulse wave sensor 110 may include a light source that emits light onto the object, and a detector that detects scattered or reflected light when light emitted by the light source is scattered or reflected from body tissue of the object such as a skin surface or blood vessels.

The light source may emit light onto the object, which is in contact with the pulse wave sensor 110. The light source may include a light emitting diode (LED), a laser diode (LD), a phosphor, and the like, but is not limited thereto. The light source may be formed of an LED, and may emit light of a single wavelength. Alternatively, the light source may be formed of an array of a plurality of LEDs, in which the LEDs may emit light of the same wavelength, or at least some of the LEDs may emit light of different wavelengths.

The detector may detect light emanating from the object as light emitted by the light source is absorbed into or scattered or reflected from the tissue of the object, and may convert the intensity of the detected light into an electric signal and output the signal. The detector may include a photo diode, a photo transistor (PTr), an image sensor (e.g., CMOS image sensor), and the like, but is not limited thereto. For example, the detector may be formed of a photo diode or an array of a plurality of photo diodes. In this case, each of the detectors may be positioned at different distances from the light source, and may detect light, emitted by the light source and scattered or reflected from the tissue of the object, at different positions.

When a user applies force to the pulse wave sensor 110 while an object is in contact with the pulse wave sensor 110 for a predetermined period of time to measure a pulse wave signal, the force sensor 120 may measure a contact force between the object and the pulse wave sensor 110. The force sensor 120 may include a piezoelectric sensor having piezoelectric properties to convert a mechanical strain of an elastic material into an electric signal. For example, the force sensor 120 may be formed of a piezo-bender, which is a plate-shaped piezoelectric sensor and generates an electric potential in response to a mechanical strain, or may be formed by series or parallel connection of the piezo-benders. In this case, the piezoelectric sensor may be based on piezoelectric ceramics such as lead zirconate titanate (PZT), or piezoelectric polymers such as polyvinylidene fluoride (PVDF) but is not limited thereto.

The processor 130 may control the pulse wave sensor 110 and the force sensor 120 to estimate bio-information. The processor 130 may be electrically connected to the pulse wave sensor 110 and the force sensor 120. The processor 130 may receive a request for estimating bio-information from a user through an input device, for example, a mechanical/electrical operation module, a touch screen, and the like. Alternatively, the processor 130 may receive the request for estimating bio-information from an external device using a communication module. Further, the processor 130 may automatically estimate the bio-information at predetermined bio-information estimation intervals.

The processor 130 may estimate the bio-information by using the pulse wave signal measured by the pulse wave sensor 110. When a pulse wave signal is measured from an object. e.g., a finger, for a predetermined period of time, a user gradually increases a pressing force while the finger is in contact with the pulse wave sensor 110. In this case, as the pressing force applied by the finger to the pulse wave sensor 110 increases, DC components of the measured pulse wave signal also increase. The processor 130 may estimate the bio-information by using the DC components of the pulse wave signal measured using oscillometry.

However, during an initial measurement interval, it may be difficult for the user to accurately control the pressing force applied by the finger to the pulse wave sensor 110, and after a predetermined time, the DC components of the pulse wave signal may be saturated even though the user increases the pressing force applied by the finger. Accordingly, if the measured pulse wave signal is used as it is, the accuracy in estimating bio-information may be reduced.

To improve the accuracy in estimating bio-information, the processor 130 may normalize the pulse wave signal. For example, the processor 130 may normalize the pulse wave signal based on contact force information measured by the force sensor 120, and may estimate the bio-information by using the normalized data, which will be described later in detail with reference to FIGS. 3A. 3B, 4A, and 4B. The bio-information to be estimated may include blood pressure, vascular age, arterial stiffness, aortic pressure waveform, vascular compliance, stress index, degree of fatigue, and the like, but is not limited thereto.

Figure 2:
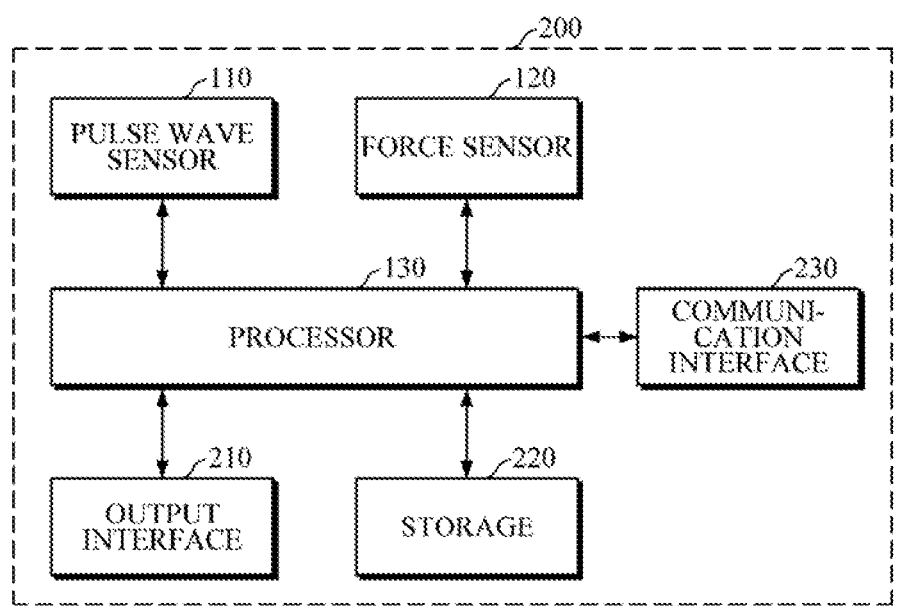
FIG. 2 is a block diagram illustrating an apparatus for estimating bio-information according to another example embodiment.

FIG. 2 is a block diagram illustrating an apparatus for estimating bio-information according to another example embodiment.

Referring to FIG. 2, a bio-information apparatus 200 for estimating bio-information according to an example embodiment may further include an output interface 210, a storage 220, and a communication interface 230, in addition to the pulse wave sensor 110, the force sensor 120, and the processor 130.

The processor 130 may control the output interface 210 to provide a variety of information, including a bio-information estimation result, to a user.

For example, upon receiving a request for estimating bio-information, the processor 130 may control the output interface 210 to provide a user with guide information for estimating bio-information. For example, the processor 130 may provide the user with guide information on a contact position, so that an object may correctly contact the pulse wave sensor 110. Further, the processor 130 may provide the user with guide information on a contact force to be applied by an object to the pulse wave sensor 110 while measuring a pulse wave signal from the object.

In addition, the processor 130 may output, through the output interface 210, the pulse wave signal measured by the pulse wave sensor 110, the contact force measured by the force sensor 120, data obtained by processing the pulse wave signal based on the contact force, a bio-information estimating result, and the like. Furthermore, the processor 130 may monitor a user's health condition based on the bio-information estimation result; and in response to the occurrence of an abnormality, the processor 130 may output warning information through the output interface 210.

In this case, the output interface 210 may include a visual output module such as a display and the like, an audio output module such as a speaker and the like, or a haptic module and the like for providing information through vibrations, tactile sensation, and the like, and may provide the user with necessary information by properly using visual/non-visual output modules.

For example, the output interface 210 may visually output guide information on a contact position and/or a contact force, which is generated by the processor 130, in the form of graphs on a display. Further, the output interface 210 may divide a display area into two or more areas, in which the output interface 210 may output the bio-information estimation result, a bio-information estimation history, and the like in a first area, and may output the pulse wave signal, the contact force information, the processed pulse wave signal information, and the like, which are used for estimating the bio-information, in a second area. In this case, the display may include a touch screen that allows touch input; and when a user selects a bio-information estimation result at a time in the bio-information estimation history, the output interface 210 may output information used for estimating bio-information at the time in the second area. However, this is merely an example, and the output of information is not limited thereto.

In addition, simultaneously with or separately from the visual output of information, the output interface 210 may provide a user with the bio-information output result or warning information by voice, vibrations, tactile sensation, and the like.

The storage 220 may store a variety of information that is used for estimating bio-information. The storage 220 may store necessary information in response to a request of the processor 130, or may provide necessary information to the processor 130.

For example, the storage 220 may store information related to estimating bio-information, e.g., the pulse wave signal measured by the pulse wave sensor 110, the contact force information measured by the force sensor 120, and a processing result of the processor 130. Further, the storage 220 may store reference information, including characteristic information of a user, such as the user's age, sex, health condition, and the like.

The storage 220 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, an optical disk, and the like, but is not limited thereto.

The processor 130 may control the communication interface 230 to transmit and receive various data to and from an external device. The external device may include a medical device such as a cuff-type blood pressure measuring device and the like, but is not limited thereto, and may include an information processing device such as a smartphone, a tablet PC, a desktop computer, a laptop computer, and the like.

The communication interface 230 may access a communication network under the control of the processor 130, or may communicate with an external device that is connected to the accessed communication network.

For example, the communication interface 230 may receive reference information, such as cuff blood pressure and a blood pressure estimation model for estimating bio-information, from an external device such as a cuff-type blood pressure measuring device. Alternatively, the communication interface 230 may transmit the pulse wave signal measured by the pulse wave sensor 110, the contact force information measured by the force sensor 120, the pulse wave signal processed by the processor 130, the bio-information estimation result, and various data to a user's mobile device such as a smartphone, a tablet PC, and the like.

The communication interface 230 may be a transceiver configured to communicate with an external device using various wired or wireless communication techniques, including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, the communication technique is not limited thereto.

Figure 3A:
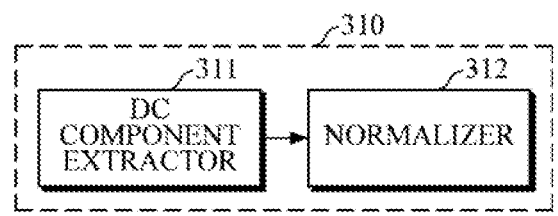
FIGS. 3A and 3B are block diagrams illustrating a configuration of a processor according to example embodiments.
Figure 3B:
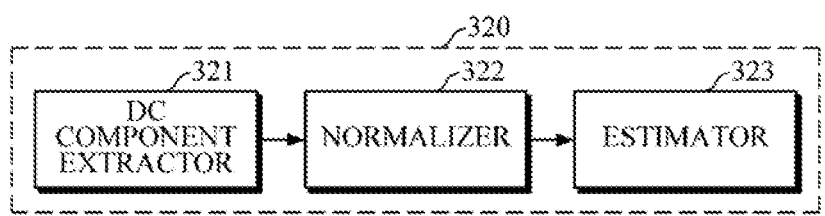
Figure 4A:
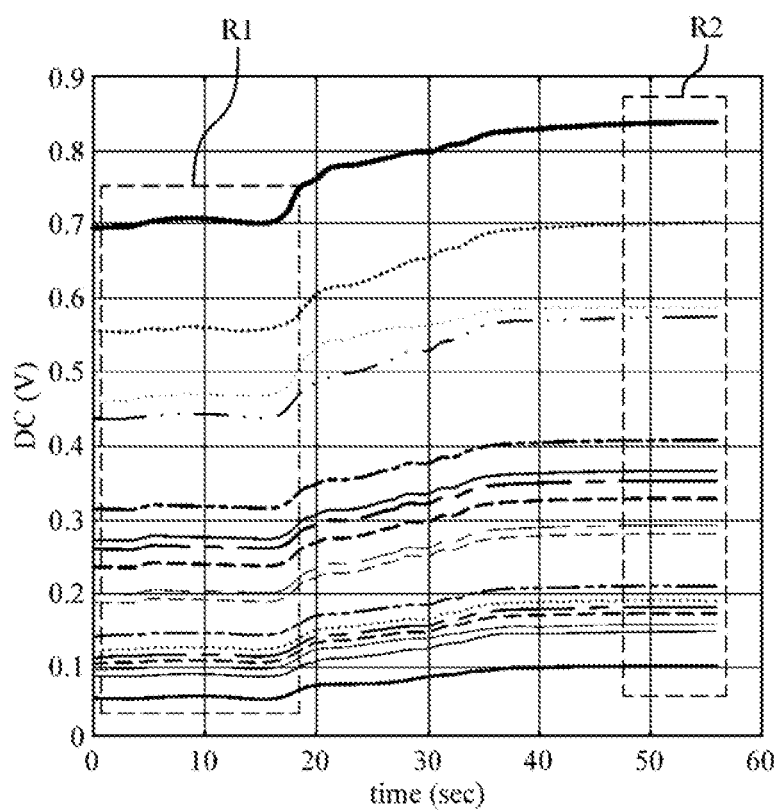
FIGS. 4A and 4B are diagrams explaining normalization of a pulse wave signal.
Figure 4B:
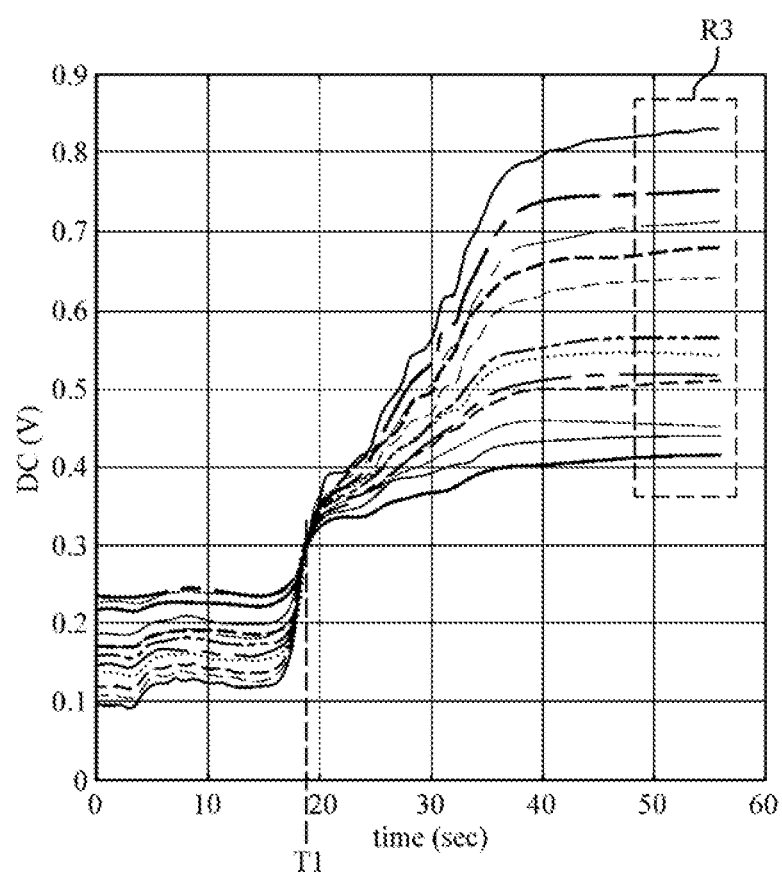

FIGS. 3A and 3B are block diagrams illustrating examples of a configuration of the processor 130 described with reference to FIGS. 1 and 2. FIGS. 4A and 4B are diagrams illustrating examples of normalization of a pulse wave signal.

Referring to FIG. 3A, a processor 310 according to an example embodiment includes a DC component extractor 311 and a normalizer 312.

Upon receiving a pulse wave signal from the pulse wave sensor 110, the DC component extractor 311 may preprocess the received pulse wave signal. For example, the DC component extractor 311 may perform preprocessing such as removing noise of the received pulse wave signal, amplifying the signal, and the like. For example, the DC component extractor 311 may perform preprocessing, such as detrending for normalizing the pulse wave signal and removing a trend and an offset, smoothing the signal, and removing high-frequency noise using a low-pass filter. Further, the DC component extractor 311 may extract DC components for use in estimating bio-information from the pulse wave signal. For example, the DC component extractor 311 may extract the DC components by passing the pulse wave signal through a low-pass filter.

FIG. 4A illustrates DC components of a pulse wave signal measured by the pulse wave sensor 110 using oscillometry. That is, FIG. 4A illustrates the DC components of each pulse wave signal detected by the pulse wave sensor 110, which is formed to have multiple channels, when a user gradually increases a contact force while an object is in contact with the pulse wave sensor 110. As illustrated in FIG. 4A, when a contact force of the object with the pulse wave sensor 110 gradually increases, the DC components of the pulse wave signal also increase. However, a wavelength path varies with each channel, and during an initial measurement interval R, it is difficult for the user to control the force applied to the pulse wave sensor 110, and during a last interval R2, the DC components are saturated even though the user increases the force applied. Accordingly, if the DC components of the pulse wave signal are used as they are in estimating bio-information, accuracy of the estimation may be reduced.

The normalizer 312 may normalize the DC components of the pulse wave signal that are extracted by the DC component extractor 311, to convert the DC components into a normalized signal for use in estimating bio-information. For example, the normalizer 312 may normalize the DC components of the pulse wave signal based on the contact force between the object and the pulse wave sensor 110, which is measured by the force sensor 120. For example, the normalizer 312 may identify a time, at which a predetermined reference force is applied, based on the contact force measured by the force sensor 120 for the DC components of each pulse wave signal, and may normalize the entire DC components using a DC component value at that time. In this case, the predetermined force may be a fixed value, (e.g., 0.5 N) that is predetermined by experiments conducted for a plurality of users or an individual user.

FIG. 4B illustrates a result obtained by normalizing DC components of a pulse wave signal of each channel using each DC component value at a time T1. In this case, the time T1 may be a time when a user starts to apply force while contacting the pulse wave sensor 110 with a finger, e.g., a time at which a force of 0.5 N is applied.

For example, as illustrated in FIG. 4B, the normalizer 312 may normalize the DC components of the pulse wave signal by dividing a DC component value of the pulse wave signal at each time by the DC component value at the time T1. In this manner, by normalizing the pulse wave signal of each channel, the normalizer 312 may normalize the DC component values of the pulse wave signal at T1 to 1. As described above, a relative magnitude of the normalized DC component values in a predetermined interval R3 may be obtained and compared to the DC component values at T1, at which a force (e.g., 0.5 N) is applied.

In another example, the normalizer 312 may normalize the DC components by subtracting the DC component values at a time at which a predetermined reference force is applied, from the DC component values at each time of the pulse wave signal. In this case, the DC component values at the time may be normalized to 0.

Referring to FIG. 3B, a processor 320 according to another example embodiment includes a DC component extractor 321, a normalizer 322, and an estimator 323, The DC component extractor 321 and the normalizer 322 are described in detail above with reference to FIG. 3A.

In this example embodiment, the estimator 323 may estimate bio-information based on the DC components of the pulse wave signal that are normalized through the processes of the DC component extractor 321 and the normalizer 322. For example, the estimator 323 may determine a DC component at a time for use in estimating bio-information among the normalized DC components of the pulse wave signal, and may estimate bio-information by using the determined DC component value.

For example, the estimator 323 may determine, as a DC component value for use in estimating bio-information, a DC component value having a maximum intensity among the normalized DC components. Referring to FIG. 4B, it can be seen that the normalized DC component values of most channels have a maximum intensity in the last interval R3. Accordingly, the estimator 323 may determine, as a DC component value for use in estimating bio-information, a DC component value of the pulse wave signal that is shown at the top of the last interval R3.

In another example, referring to FIG. 4B, the estimator 323 may determine, as a DC component value for use in estimating bio-information, a DC component value at a time when a predetermined time elapses after the time T1, at which a predetermined reference force is applied. In this case, the time when a predetermined time elapses after the time T1 may be set equally for all users, or may be set differently for each user by reflecting personal characteristics of each individual user.

In another example, referring to FIG. 4B, the estimator 323 may determine, as a DC component value for use in estimating bio-information, a DC component value at a time at which a predetermined force is applied after the time T, when the predetermined reference force is applied; i.e., a time at which, after the object presses the pulse wave sensor 110 with a reference force, the force increases to reach a predetermined force. In this case, the time, at which the predetermined force is applied after the time T1, when the reference force is applied, may be set equally for all users, or may be set differently for each user by reflecting personal characteristics of each individual user.

In another example, the estimator 323 may determine, as a DC component value for use in estimating bio-information, the normalized DC component value corresponding to a point at which an amplitude of the measured pulse wave signal is a maximum. Once the pulse wave signal is measured, the estimator 323 may obtain AC components of the pulse wave signal, and may determine a time, at which an amplitude of the AC components is maximum, in the AC components.

Several example embodiments of determining the normalized DC component values for use in estimating bio-information are described above, but the present disclosure is not limited thereto.

When the pulse wave sensor 110 is formed to have multiple channels to measure a plurality of pulse wave signals, the estimator 323 may select any one pulse wave signal for use in estimating bio-information. For example, the estimator 323 may select any one pulse wave signal based on a variety of information, such as, but not limited to, a maximum amplitude value and a minimum amplitude value of the pulse wave signal, a difference between the maximum amplitude value and the minimum amplitude value, a relative magnitude of the normalized DC component values at a time compared to a time when a reference force is applied, and the like, and may estimate bio-information based on the normalized DC components of the selected pulse wave signal.

Alternatively, the estimator 323 may determine a DC component value for use in estimating bio-information by combining DC component values at the determined time among the normalized DC components of each channel as described above. In this case, the estimator 323 may determine some pulse wave signals based on the variety of information as described above, and may also determine a DC component value for use in estimating bio-information by combining the normalized DC components of the determined pulse wave signals.

Upon determining the DC component value for use in estimating bio-information, as described above, the estimator 323 may input the determined DC component value into a predetermined bio-information estimation model, and may obtain a result of the bio-information estimation model as an estimated bio-information value. For example, the following Equation 1 is a linear function of the bio-information estimation model. However, the bio-information estimation model is not limited thereto, and may be defined in various manners by linear/nonlinear regression analysis, neural network, deep learning, and the like.

$$y=ax+b \qquad \text{[Equation 1]}$$

Herein, y denotes an estimated bio-information value; x denotes a DC component value for use in estimating bio-information; a and b are values predefined through preprocessing, and may be defined differently according to types of bio-information, e.g., systolic blood pressure and diastolic blood pressure.

The estimator 323 may determine, as the DC component value for use in estimating bio-information, two or more DC component values among the normalized DC components. For example, as described above, the estimator 323 may determine two or more times by combining one or more of various criteria for determining DC component values for use in estimating bio-information, and may use the DC component values at each of the times in estimating bio-information.

For example, the estimator 323 may determine, as the DC component value for use in estimating bio-information, a DC component value at a predetermined time after the time when the reference force is applied and a DC component value at a time when an amplitude of the pulse wave signal is a maximum. In another example, the estimator 323 may determine, as the DC component value for use in estimating bio-information, DC components at a time when a first force is applied and at a time when a second force is applied after the time when the reference force is applied. In another example, the estimator 323 may determine, as the DC component value for use in estimating bio-information, a DC component value at the time when the first force is applied, and a DC component value having a maximum intensity. In another example, the estimator 323 may determine, as the DC component value for use in estimating bio-information, a DC component value at a time when an amplitude of the pulse wave signal is at a maximum, the DC component value having the maximum intensity, and a DC component value at a time when a predetermined force is applied. Alternatively, the estimator 323 may determine, based on a plurality of DC component values for use in estimating bio-information, DC component values of a first pulse wave signal and a second pulse wave signal, which are determined based on various criteria described above, but the DC component values are not limited thereto.

In this case, the estimator 323 may assign a weight to each of the determined DC component values, and may combine the weighted DC component values by using, for example, the following Equation 2, and then the estimator 323 may input the combination result into Equation 1.

$$x = \alpha_1 x_1 + \alpha_2 x_2 + \ldots + \alpha_n x_n \quad \text{[Equation 2]}$$

Herein, x denotes a value input into the bio-information estimation model, and may be a value obtained by combining DC component values $x_1, x_2, \ldots,$ and $x_n$; and $\alpha_1, \alpha_2, \ldots$ and $\alpha_n$ that denote weights assigned to each of the DC component values.

Further, the estimator 323 may obtain an additional feature, in addition to the aforementioned DC component values, and may estimate bio-information by further using the obtained additional feature. In this case, the bio-information estimation model may be predefined as a function using the DC component values and the additional feature as input values.

The estimator 323 may obtain the additional feature by analyzing a waveform of a pulse wave signal. In this case, an example of the additional feature may include a force value applied by the object to the pulse wave sensor at a time when an amplitude of the pulse wave signal is a maximum. However, the additional feature is not limited thereto, and the estimator 323 may extract features, associated with cardiac output, total peripheral resistance, and the like, that affect blood pressure, for estimating blood pressure. For example, the estimator 323 may obtain one or more of the measurements of heartbeat information, a shape of a waveform, a time and an amplitude of a maximum point, a time and an amplitude of a minimum point, and amplitude and time information of pulse waveform components constituting the pulse wave signal, from the pulse wave signal, and may obtain features by properly combining the obtained information.

Figure 5A:
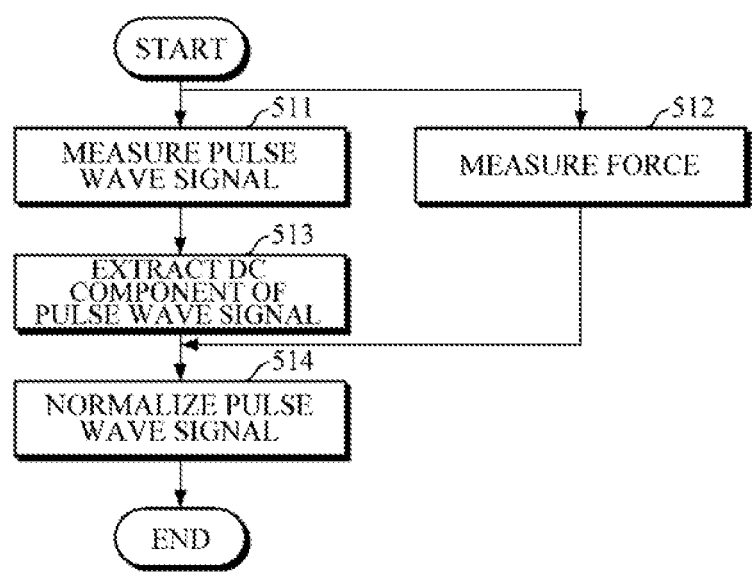
FIG. 5A is a flowchart illustrating a method of normalization for estimating bio-information according to an example embodiment.

FIG. 5A is a flowchart illustrating a method of normalization for estimating bio-information according to an example embodiment.

FIG. 5A may be an example performed by the apparatuses 1M and 200 for estimating bio-information according to the example embodiments of FIGS. 1 and 2.

The apparatuses 100 and 200 for estimating bio-information may measure a pulse wave signal in operation 511. The pulse wave sensor 110 may measure the pulse wave signal from an object for a predetermined period of time. In this case, the object may be a body part such as the back of the hand, the wrist, fingers, and the like, at which veins or capillaries are located.

Before and/or during measurement, the apparatuses 100 and 200 for estimating bio-information may display guide information for a user, to accurately measure the pulse wave signal from the object. For example, the apparatuses 100 and 200 for estimating bio-information may output an image showing a state, in which a finger correctly contacts a contact surface of the pulse wave sensor, through a display. Further, the apparatuses 100 and 200 for estimating bio-information may output a notification (e.g., beep sound, mark that blinks on the display, etc.) for notifying the beginning of a measurement, and may output a pressing force, to be applied by a finger for a predetermined period of time, in the form of graphs. However, the guide information is not limited thereto.

In addition, the apparatuses 100 and 200 for estimating bio-information may measure a force, applied by the object to the pulse wave sensor, while measuring the pulse wave signal, by using a force sensor 120, in operation 512.

Then, the apparatuses 100 and 200 for estimating bio-information may extract DC components in operation 513 from the pulse wave signal measured in operation 511. For example, the apparatuses 100 and 200 for estimating bio-information may obtain the DC components by passing the measured pulse wave signal through a low-pass filter. In this case, the apparatuses 100 and 200 for estimating bio-information may perform preprocessing, such as amplifying the measured pulse wave signal, removing noise and smoothing the pulse wave signal, and the like.

Subsequently, the apparatuses 100 and 200, for estimating bio-information, may normalize the extracted DC components of the pulse wave signal in operation 514. For example, there is a predetermined correlation between the DC components of the pulse wave signal and the pressing force applied by the object to the pulse wave sensor 110. However, during an initial measurement interval, it may be difficult for a user to accurately control the pressing force applied by the finger to the pulse wave sensor 110, and after the force is increased, the DC components of the pulse wave signal become saturated. Thus, if the DC components of the measured pulse wave signal are used as they are in this example embodiment, the accuracy in estimating bio-information may be reduced, as described above.

Accordingly, by normalizing the DC components of the pulse wave signal, and using the normalized DC components of the pulse wave signal in estimating bio-information, the apparatuses 100 and 200 for estimating bio-information may obtain bio-information estimation result more accurately. For example, the apparatuses 100 and 200 for estimating bio-information may determine a time at which a predetermined force is applied, based on force information measured in operation 512, and may normalize the entire DC component values based on the DC component value at the determined time. For example, the apparatuses 100 and 200 for estimating bio-information may normalize the DC components of the pulse wave signal by dividing the DC component value at each time of the entire DC component by the DC component value at the determined time, or by subtracting the DC component value at the determined time from the DC component value at each time of the entire DC component. However, the normalization is not limited thereto. As described above, by normalizing the DC components, the apparatuses 100 and 200 for estimating bio-information may obtain a relative magnitude of the DC component values after a predetermined time, compared to the DC component values at the determined time.

The apparatuses 100 and 200 for estimating bio-information may store the normalized DC components in the storage 220, may output the normalized DC components through the output interface 210, or may transmit the normalized DC components to an external device through the communication interface 230.

Figure 5B:
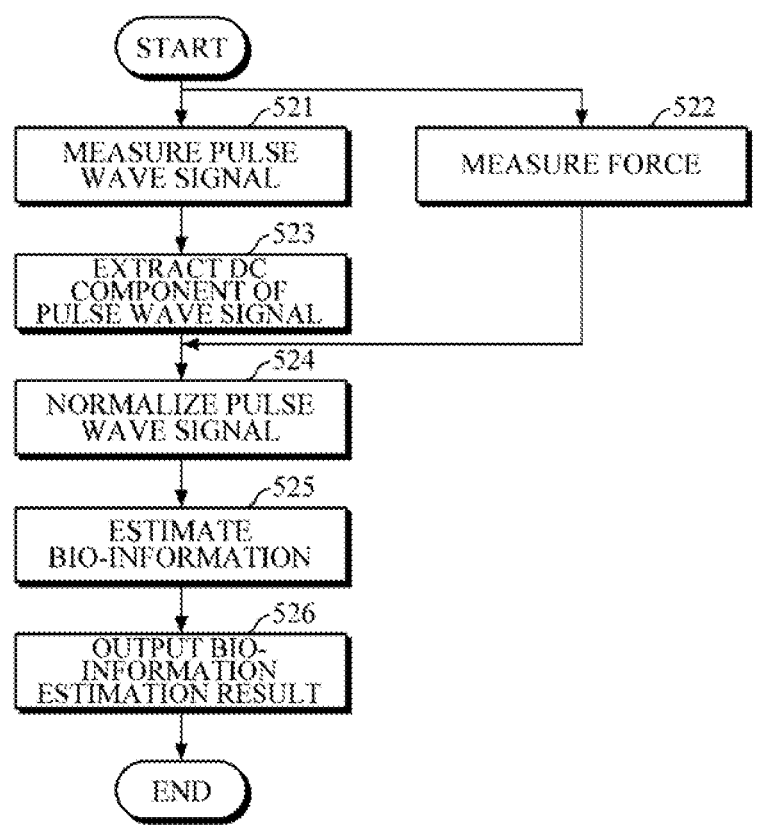
FIG. 5B is a flowchart illustrating a method of estimating bio-information according to an example embodiment.

FIG. 5B is a flowchart illustrating a method of estimating bio-information according to an example embodiment.

The method of FIG. 5B may be an example performed by the apparatuses 100 and 200 for estimating bio-information according to the example embodiments of FIGS. 1 and 2.

The apparatuses 100 and 200 for estimating bio-information may measure a pulse wave signal in operation 521, and at the same time, may measure a force applied by the object to the pulse wave sensor in operation 522.

Then, the apparatuses 100 and 200 for estimating bio-information may extract DC components from the measured pulse wave signal in operation 523. As described above, the apparatuses 100 and 200 for estimating bio-information may extract the DC components by using a low-pass filter, and may perform other necessary preprocessing operations.

Subsequently, the apparatuses 100 and 200 for estimating bio-information may normalize the extracted DC components of the pulse wave signal in operation 524. As described above, the apparatuses 100 and 200 for estimating bio-information may identify a time, at which a predetermined force is applied, based on force information measured in operation 522, and may normalize the entire DC component by using a DC component value at the time. In this case, for example, the apparatuses 100 and 200 for estimating bio-information may normalize the DC components by dividing the DC component value at each time of the entire DC component by the DC component value at a time when a predetermined force is applied. In another example, the bio-information estimating apparatuses 100 and 200 may normalize the DC components by subtracting the DC component value at the time when the predetermined force is applied from the DC component value at each time of the entire DC component.

Next, the apparatuses 100 and 200 for estimating bio-information may estimate bio-information in operation 525 by using the normalized DC components of the pulse wave signal, which are normalized in operation 524.

For example, the apparatuses 100 and 200 for estimating bio-information may determine, as a DC component value for use in estimating bio-information, any one or a combination of two or more of: (1) the normalized DC component values having a maximum intensity, (2) the normalized DC component value at a time when a predetermined time elapses after a time when a reference force is applied, (3) the normalized DC component value at a time when a predetermined force is applied after the time when the reference force is applied, and (4) the normalized DC component value corresponding to a point at which an amplitude of the pulse wave signal is maximum. Upon determining the DC component value for use in estimating bio-information, as described above, the apparatuses 100 and 200 for estimating bio-information may obtain an estimated bio-information value by applying the determined DC component value to a bio-information estimation model.

The bio-information estimation model may be pre-defined according to types of bio-information, and may be defined as a linear/non-linear equation by using various methods, such as linear/nonlinear regression analysis, neural network, deep learning, and the like.

The apparatuses 100 and 200 for estimating bio-information may obtain an additional feature as described above, and may also estimate bio-information by combining the obtained additional feature with the normalized DC value.

Then, the apparatuses 100 and 200 for estimating bio-information may output a bio-information estimation result and may provide the estimation result for a user in operation 526. In this case, the apparatuses 100 and 200 for estimating bio-information may output the bio-information estimation result through a display, a speaker, a haptic module, and the like, which are mounted on another device or am connected thereto by wire or wirelessly.

Figure 6:
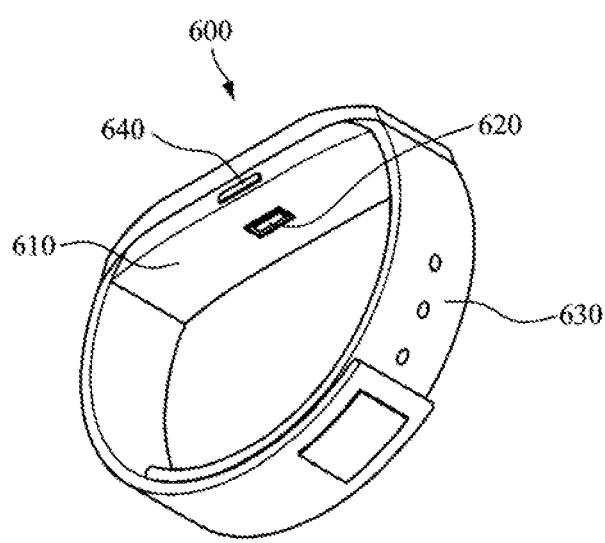
FIG. 6 is a diagram illustrating a wearable device according to an example embodiment.

FIG. 6 is a diagram illustrating a wearable device worn on a wrist according to an example embodiment. Various example embodiments of the aforementioned apparatuses 100 and 200 for estimating bio-information may be mounted in a smart watch worn on a wrist or a smart band-type wearable device, but the apparatus for estimating bio-information is not limited thereto.

Referring to FIG. 6, the wearable device 600 includes a main body 610 and a strap 630.

The main body 610 may be formed to have various shapes, and may include modules which are mounted inside or outside of the main body 610 to perform the aforementioned function of estimating bio-information, as well as various other functions (e.g., time, alarm, etc.). A battery may be embedded in the main body 610 or the strap 630 to supply power to various modules of the wearable device 600.

The strap 630 may be connected to the main body 610. The strap 630 may be flexible so as to be wrapped around a user's wrist. The strap 630 may be bent in a manner that allows the strap 630 to be detached from the user's wrist or may be formed as a band that is not detachable. Air may be injected into the strap 630 or an airbag may be included in the strap 630, so that the strap 630 may have elasticity according to a change in pressure applied to the wrist, and the change in pressure of the wrist may be transmitted to the main body 610.

The main body 610 may include a pulse wave sensor 620 for measuring a pulse wave signal. When the main body 610 is worn on a user's wrist, the pulse wave sensor 620 may be mounted on one surface of the main body 610 which comes into contact with the user's wrist. The pulse wave sensor 620 may include a light source for emitting light to the wrist and a detector for detecting light scattered or reflected from body tissue, such as a skin surface, blood vessels, and the like.

Further, a force sensor, which measures a contact force between the wrist and the contact surface of the pulse wave sensor 620, may be mounted inside the main body 610, i.e., in a predetermined position opposite the contact surface of the pulse wave sensor 620 which comes into contact with the user's wrist. The user may change the contact force between the wrist and the pulse wave sensor 620 by moving the main body 610 to a thicker part of the user's arm, or by using the finger, palm, and the like of the other hand, on which the main body 610 is not worn.

In addition, a processor may be mounted in the main body 610, and may be electrically connected to the various modules of the wearable device 600 to control operations thereof.

The processor may estimate bio-information by using the pulse wave signal measured by the pulse wave sensor 620 and the contact force information measured by the force sensor 120. Once the pulse wave sensor 620 measures the pulse wave signal, the processor may extract DC components from the pulse wave signal, and may estimate bio-information by using the extracted DC components. In this case, the processor may normalize the DC components of the pulse wave signal based on force information measured by the force sensor 120, and may estimate bio-information by using the normalized DC components.

For example, the processor may normalize the DC components by dividing the DC component value at each time of the entire DC component of the pulse wave signal by the DC component value at a time when a predetermined force is applied, or by subtracting the DC component value at the time from the DC component value at each time of the entire DC component of the pulse wave signal. The processor may obtain one or more DC component values according to predetermined criteria among the normalized DC components of the pulse wave signal, and may estimate bio-information by applying a bio-information estimation model to the obtained DC component values.

In response to a request for estimating bio-information, the processor may output guide information for estimating bio-information to a user through a display.

The display may be mounted on a front surface of the main body 610, and may include a touch panel for touch input. The display may receive a touch input from a user, may transmit the received touch input to the processor, and may display a processing result of the processor. For example, the display may display an estimated bio-information value, and may display additional information, such as a bio-information estimation history, a change in health condition, warning information, and the like, along with the estimated value.

A storage, which stores the processing result of the processor and a variety of information, may be mounted in the main body 610. In this case, the variety of information may include information related to estimating bio-information, as well as information related to other functions of the wearable device 600.

In addition, the main body 610 may include a manipulator 640 which receives a user's instruction and transmits the received instruction to the processor. The manipulator 640 may include a power button to input an instruction to turn on/off the wearable device 600.

Moreover, a communication interface, which communicates with an external device, may be mounted in the main body 610. The communication interface may transmit a bio-information estimation result to an external device, to output the estimation result through the external device, e.g., an output module of a user's mobile terminal, or to store the estimation result in a storage module of the external device. Furthermore, the communication interface may receive information for supporting various other functions of the wearable device and the like from the external device.

Figure 7:
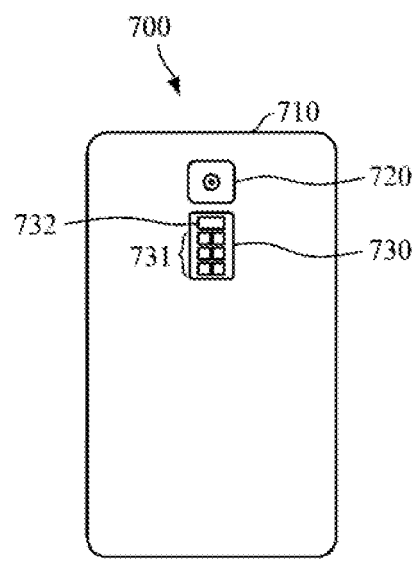
FIG. 7 is a diagram illustrating a smart device according to an example embodiment.

FIG. 7 is a diagram illustrating a smart device, to which the aforementioned example embodiments of the apparatus for estimating bio-information are applied. In this case, the smart device may be a smartphone and a tablet PC, but is not limited thereto.

Referring to FIG. 7, the smart device 700 may include a main body 710 and a pulse wave sensor 730 formed on one surface of the main body 710. The pulse wave sensor 730 may include one or more light sources 731 and a detector 732. As described above, the pulse wave sensor 730 may be mounted on a rear surface of the main body 710, but is not limited thereto, and may be configured in combination with a fingerprint sensor or a touch panel mounted on a front surface of the main body 710.

Further, a force sensor may be included in the main body 710. When a user touches the pulse wave sensor 730 with a finger and the like and applies force thereto, the force sensor 120 may measure the force and may transmit the force to the processor.

A display may be mounted on a front surface of the main body 710, The display may visually display a bio-information estimation result and the like. The display may include a touch panel, and may receive a variety of information input through the touch panel and transmit the received information to the processor.

Moreover, an image sensor 720 may be mounted in the main body 710. When a user's finger approaches the pulse wave sensor 730 to measure a pulse wave signal, the image sensor 720 may capture an image of the finger and may transmit the captured image to the processor. In this case, based on the image of the finger, the processor may identify a relative position of the finger with respect to an actual position of the pulse wave sensor 730, and may provide the relative position of the finger to the user through the display, to guide a user to accurately contact the pulse wave sensor 730 with the finger.

The processor may estimate bio-information by using the pulse wave signal measured by the pulse wave sensor 730. As described above, the processor may normalize DC components of the pulse wave signal by using force information measured by the force sensor 120, and may estimate bio-information by using the normalized DC components of the pulse wave that is described above in detail.

The embodiments can be realized as a computer-readable code written on a non-transitory computer-readable recording medium. The computer-readable recording medium may be any type of recording device in which data is stored in a computer-readable manner.

Examples of the non-transitory computer-readable recording medium include a ROM, a RAM, a CD-ROM, a magnetic tape, a floppy disc, an optical data storage, and a carrier wave (e.g., data transmission through the Internet). The non-transitory computer-readable recording medium can be distributed over a plurality of computer systems connected to a network so that a computer-readable code is written thereto and executed therefrom in a decentralized manner. Functional programs, codes, and code segments for realizing the embodiments can be readily deduced by one of ordinary skill in the art.

The inventive concepts have been described herein with regard to the example embodiments. However, it will be obvious to those skilled in the art that various changes and modifications can be made without changing technical conception and features of the present disclosure. Thus, it is clear that the above-described example embodiments are illustrative in all aspects and are not intended to limit the present disclosure.

What is claimed is:

1. An apparatus for estimating bio-information, the apparatus comprising:
a pulse wave sensor configured to measure a pulse wave signal from an object, for a predetermined period of time; and
a processor configured to:
obtain a predetermined reference force;
extract direct current (DC) components of the pulse wave signal measured for the predetermined period of time, and
normalize each extracted DC component for the predetermined period of time, based on a measurement of a corresponding extracted DC component at a time instant when the predetermined reference force is applied by the object to the pulse wave sensor, and
estimate the bio-information, based on the normalized DC components.

2. The apparatus of claim 1, wherein the pulse wave sensor comprises:
a light source configured to emit light onto the object; and
a detector configured to detect light that is reflected from the object.

3. The apparatus of claim 1, further comprising a force sensor configured to measure a force that is applied by the object to the pulse wave sensor, for the predetermined period of time.

4. The apparatus of claim 1, wherein the processor is further configured to extract the DC components by passing the measured pulse wave signal through a low-pass filter.

5. The apparatus of claim 1, wherein the processor is further configured to normalize the extracted DC components by dividing the extracted DC components of the pulse wave signal measured at each time during the predetermined period of time by each of the extracted DC components of the pulse wave signal measured at the time instant when the predetermined reference force is applied.

6. The apparatus of claim 1, wherein the processor is further configured to normalize the extracted DC components by subtracting each of the extracted DC components of the pulse wave signal measured at the time instant when the predetermined reference force is applied from the extracted DC components of the pulse wave signal measured at each time during the predetermined period of time.

7. The apparatus of claim 1, wherein the processor is further configured to estimate the bio-information, based on the normalized DC components and a bio-information estimation model.

8. The apparatus of claim 7, wherein the bio-information comprises any one or any combination of a blood pressure, a vascular age, an arterial stiffness, an aortic pressure waveform, a vascular compliance, a stress index, and a degree of fatigue.

9. The apparatus of claim 7, wherein the processor is further configured to:
determine at least one DC component among the normalized DC components, and
estimate the bio-information, using the at least one determined DC component.

10. The apparatus of claim 9, wherein the processor is further configured to determine, among the normalized DC components, as a DC component for use in estimating the bio-information, any one or any combination of a DC component having a maximum intensity, a DC component at a predetermined time after the time instant when the predetermined reference force is applied, a DC component at a time when a predetermined force is applied after the time instant when the predetermined reference force is applied, and a DC component corresponding to a point at which an amplitude of the measured pulse wave signal is at a maximum.

11. The apparatus of claim 10, wherein the processor is further configured to estimate the bio-information, using a force value applied by the object to the pulse wave sensor at the time when the amplitude of the measured pulse wave signal is at the maximum.

12. The apparatus of claim 1, wherein the processor is further configured to guide either one or both of a position of the pulse wave sensor to be contacted by the object, and a force to be applied by the object to the pulse wave sensor for the predetermined period of time.

13. The apparatus of claim 1, further comprising an output interface configured to output the estimated bio-information.

14. A method of estimating bio-information, the method comprising:
obtaining a predetermined reference force;
measuring a pulse wave signal from an object, for a predetermined period of time;
extracting direct current (DC) components of the pulse wave signal measured for the predetermined period of time;
normalizing each extracted DC component over the predetermined period of time, based on a measurement of a corresponding extracted DC component at a time instant when the predetermined reference force is applied by the object to a pulse wave sensor; and
estimating the bio-information, based on the normalized DC components.

15. The method of claim 14, further comprising measuring a force that is applied by the object to the pulse wave sensor, for the predetermined period of time.

16. The method of claim 14, wherein the obtaining of the normalized DC components comprises normalizing the extracted DC components by dividing the extracted DC components of the pulse wave signal measured at each time during the predetermined period of time by each of the extracted DC components of the pulse wave signal measured at the time instant when the predetermined reference force is applied.

17. The method of claim 14, wherein the obtaining of the normalized DC components further comprises normalizing the extracted DC components by subtracting each of the extracted DC components of the pulse wave signal measured at the time instant when the predetermined reference force is applied from the extracted DC components of the pulse wave signal measured at each time during the predetermined period of time.

18. The method of claim 14, further comprising estimating the bio-information, based on the normalized DC components and a bio-information estimation model.

19. The method of claim 18, wherein the estimating of the bio-information comprises:
determining at least one DC component among the normalized DC components; and
estimating the bio-information, using the at least one determined DC component.

20. The method of claim 19, wherein the determining of the at least one DC component comprises determining, among the normalized DC components, as a DC component for use in estimating the bio-information, any one or any combination of a DC component having a maximum intensity, a DC component at a predetermined time after the time instant when the predetermined reference force is applied, a DC component at a time when a predetermined force is applied after the time instant when the predetermined reference force is applied, and a DC component corresponding to a point at which an amplitude of the measured pulse wave signal is at a maximum.

21. The method of claim 20, wherein the estimating of the bio-information further comprises estimating the bio-information, using a force value applied by the object to the pulse wave sensor at the time when the amplitude of the measured pulse wave signal is at the maximum.

22. A non-transitory computer-readable storage medium comprising instructions to cause a processor to:
    obtain a predetermined reference force;
    measure a force that is applied by an object to a pulse wave sensor, for a predetermined period of time;
    measure a pulse wave signal from the object, for the predetermined period of time, using the pulse wave sensor;
    extract DC components of the pulse wave signal measured for the predetermined period of time;
    normalize each extracted DC component over the predetermined period of time, based on a measurement of a corresponding extracted DC component at a time instant when the predetermined reference force is applied by the object to the pulse wave sensor;
    estimate bio-information, based on the normalized DC components; and
    output the estimated bio-information.

23. The non-transitory computer-readable storage medium of claim 22, wherein the instructions further cause the processor to:
    monitor a health condition of a user, based on the estimated bio-information; and
    output warning information, based on the monitored health condition.

24. The non-transitory computer-readable storage medium of claim 22, wherein the instructions further cause the processor to:
    capture an image of the object, using an image sensor;
    based on the captured image, identify a relative position of the object with respect to an actual position of the pulse wave sensor; and
    provide the identified relative position of the object, to guide a user to contact the pulse wave sensor with the object.

* * * * *